United States Patent [19]

Medgyesy et al.

[11] Patent Number: 4,784,957
[45] Date of Patent: Nov. 15, 1988

[54] PROCESS FOR THE PROMOTION OF REGENERATION OF PLANTS FROM TISSUE CULTURES

[75] Inventors: Péter Medgyesy; László Márton; László Purhauser, all of Szeged, Hungary

[73] Assignee: Richter Gedeon Vegyeszeti Gyar RT., Budapest, Hungary

[21] Appl. No.: 687,607

[22] Filed: Dec. 31, 1984

[30] Foreign Application Priority Data

Dec. 30, 1983 [HU] Hungary ............................. 4524/83

[51] Int. Cl.$^4$ ......................... C12N 5/00; C12N 5/02
[52] U.S. Cl. ............................... 435/240.4; 435/240.5; 435/240.54
[58] Field of Search ............... 435/240, 241, 240.4, 435/240.5, 240.54

[56] References Cited

PUBLICATIONS

Gavinlertuatana et al. 1980 "Control of Ethylene Synthesis and Action by Silver Nitrate . . . " *J Am Soc Hort Sci* (Abstract) v105(3) 304–7.
Miller et al. 1984 "Ethylene Biosynthesis and Xylogenesis in *Lactuca Sativa* . . . " *J Exp Bot* (Abstract) v 35 691–98.
Conger 1981 *Cloning Agricultural Plants Via In Vitro Techniques* CRC Press pp. 108–123.
Street 1974 *Tissue Culture and Plant Science* Academic Press pp. 219–220, 229–231.
Lau et al. 1976, Chem. Abstr. 85 (17): #119661m.
Green et al. 1975, Crop Sci, 15: 417–421.
Gavinlertvatana et al. 1980, J. Amer. Hort. Sci, 105(3): 304–307.
Beyer, Plant Physiol. vol. 63, pp. 169–174 (1979).
What's New in Plant Physiology, vol. 12, pp. 37–40 (1981).
The Control of Growth and Differentiation in Plants, Wareing, P. F. et al., pp. 1–2, (Pergamon Press 1970).

*Primary Examiner*—Charles F. Warren
*Assistant Examiner*—David T. Fox
*Attorney, Agent, or Firm*—Herbert Dubno; Jonathan Myers

[57] ABSTRACT

The invention relates to a process for the promotion of regeneration of differentiated plants from vegetable cells maintained in tissue cultures by adding inhibitors of ethylene production or ethylene action to the hormone-containing or hormone-free culture medium used for maintaining the tissue cultures. The process is equally suitable for the promotion of the regeneration of mono- and dicotyledons. As an inhibitor preferably silver nitrate or cobalt chloride is employed.

9 Claims, 3 Drawing Sheets

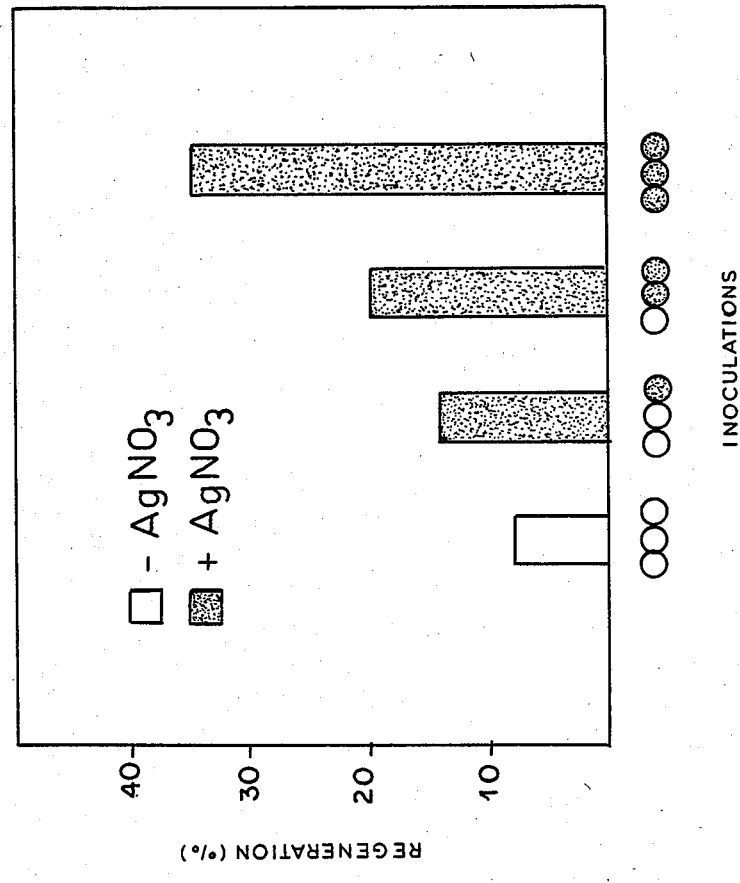

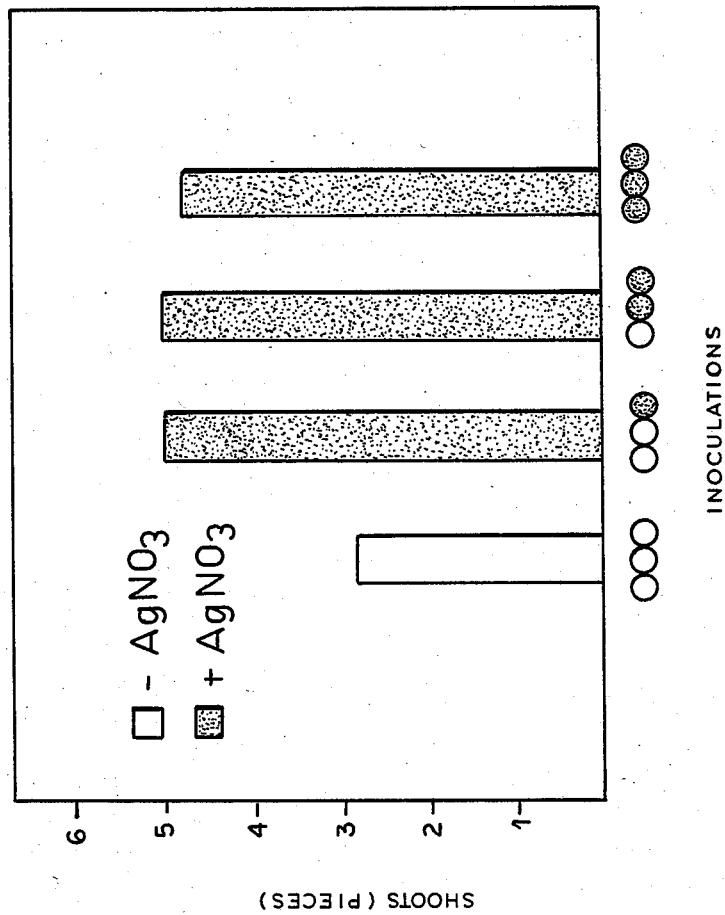

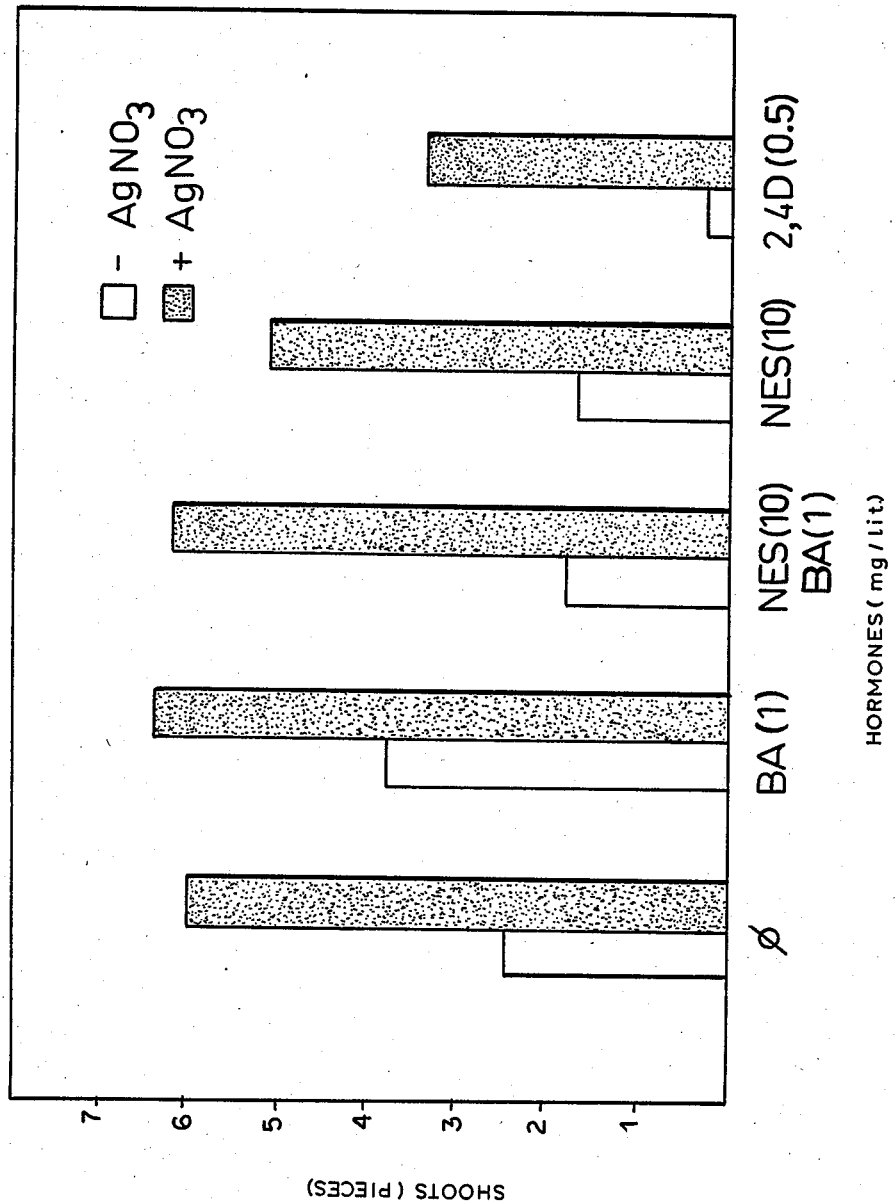

PROCESS FOR THE PROMOTION OF REGENERATION OF PLANTS FROM TISSUE CULTURES

The invention relates to a process for the promotion of plant regeneration from tissue cultures.

In the last decade cell genetics and the experiments on cultivation of vegetable tissues have produced numerous promising results, because of new, effective techniques for example for mutant isolation, somatic hybridization, cytoplasm transfer. Their practical application is, however, strongly limited by the fact that in the tissue cultures of monocotyledons, which are of utmost importance economically, so far only the most fundamental methods of tissue cultivation could be employed.

The main problems in connection with cultivation of monocotyledons in tissue cultures are as follows:

(a) tissue cultures can be initiated only from vegetable parts capable of functional cell division (embryo, immature inflorescence, young leaf parts);

(b) in the undifferentiated tissue parts (calli) there is no chlorophyll formation, i.e. calli are white;

(c) the plant regeneration from tissue culture either via organogenesis or via embryogenesis is incidental, and this ability is rapidly lost during subsequent inoculations or is preserved merely in certain genotypes [Vasil, I. K., Plant improvement and somatic cell genetics, Academic Press: New York, 179–203 (1982)].

Following the strategy working well for dicotyledons numerous hormones and hormone combinations have been tested to solve this problem without any essential result [Dudits, D. et al., Can. J. Bot. 53, 957–963 (1975)]. According to the most usable process, from immature embryo callus was induced in the presence of 1 kg/lit. of 2,4-D (2,4-dichlorophenoxyacetic acid, a hormone of the auxin type), from which parallel with the withdrawal of the hormone, through organogenesis or embryogenesis plant could be regenerated [Sears, R. G. et al., Crop. Sci. 22, 546–550 (1982)]. The process is disadvantageous in that the calli must be injected into media with gradually decreasing 2,4-D content, therefore, the process is cumbersome and takes a long time. In millet varieties plants could be regenerated from calli of protoplast origin through embryogenesis [Vasil, I. K.: Plant improvement and somatic cell genetics, Academic Press: New York, 233–252 (1983)] but about 90 to 99% of the embryoids did not get beyond the sprout homozygote state.

In the case of dicotyledons generally satisfactory results are achieved with various hormone combinations, but in older cultures and in the case of hybrids with higher chromosome numbers the regeneration ability is substantially decreased.

The principal source of the problems is that the auxins, which promote cell division in a certain concentration effectively, in higher concentrations have an inhibiting effect, moreover, their regeneration and greening in-hibiting activity is also known. It may, therefore, be presumed that the the incapability of monocotyledon cells of cell division and the poor regeneration and greening ability of certain tissue cultures of mono- and dicotyledons are the consequence of the high endogenous auxin level.

Recently it has also been reported that in non-regenerating calli cultivated on culture media with high auxin concentrations high ethylene levels can be detected. From this it was concluded that ethylene production can be used as an early index of severe stress caused by auxins. It was further suggested that the regeneration problems can be solved by reducing the auxin concentration, i.e. by adding antiauxins to the tissue cultures [Huxter, T. J. et al.: Physiol. Plant. 53, 319–326 (1981); Grady, K. L. et al.: Plant. Physiol. 70, 919–921 (1982); Garcia, F. G. et al.: Ann. Bot. 51, 207–295 (1983)].

The addition of antiauxins generally proved, however, ineffectual, since experiments showed that antiauxins (e.g. TIBA) merely have a strong growth inhibiting effect in tissue cultures.

Our intention was to provide a method by which plants (both mono- and dicotyledons) can be regenerated from tissue cultures considerably more efficiently than by the hitherto known techniques.

Our invention is based on the surprising recognition that the regeneration ability can substantially be improved by adding inhibitors of ethylene production or ethylene action to hormone-containing or hormone-free culture media used for maintaining vegetable tissue cultures. In other words, we have surprisingly found that the desired increase of regeneration ability can be achieved also in the presence of hormones (auxins) by using inhibitors of ethylene production or ethylene action. We have further found that inhibitors of ethylene production or ethylene action, unlike antiauxins, have no adverse effect on plant growth.

Accordingly, the invention relates to a process for the promotion of regeneration of differentiated plants from vegetable cells maintained in tissue cultures by adding inhibitors of ethylene production or ethylene action to the hormone-containing or hormone-free culture medium used for maintaining the tissue cultures.

The inhibitors of ethylene production are chemical substances, which inhibit ethylene synthesis, while the inhibitors of ethylene action act in a competitive manner.

There are numerous inhibitors of ethylene production and ethylene action known in the art [see e.g.: What's new in plant physiology, 12, 37–40 (1981)]. Such inhibitors include for example $AgNO_3$, $CoCl_2$, $CO_2$ and various organic compounds such as dinitrophenol, 2,5-norbornadiene, etc. It has been found that any of these inhibitors can successfully be employed in the process according to the invention.

The process according to the invention is suitable for the promotion of regeneration of a wide range of mono- and dicotyledonous plants, e.g. cereals, tobacco and other cultivated plants. Accordingly, when carrying out the process of the invention one can start both from tissue cultures of monocotyledons and from those of dicotyledons.

Of the inhibitors $AgNO_3$ and $CoCl_2$ are particularly preferred. The inhibitor concentration may be varied within a wide range, and strongly depends on the chemical entity of ethylene inhibitor, on the plant to be regenerated, on its pretreatment, etc. The determination of the optimum concentration is the task of a person skilled in the art, and the proper concentration should always be selected considering all circumstances.

The inhibitors of ethylene production or ethylene action can be added directly to the culture medium used for maintaining plant cells (hormone-containing culture medium) or alternatively, the callus culture may previously be placed into a hormone-free culture medium.

According to a preferred embodiment of the process the inhibitor is added to a hormone-free culture medium. The culture medium may be any medium conventionally used for the cultivation of plant tissues, and generally contains as main components a carbon source, mineral salts and optionally growth promoters, e.g. vitamins and hormones.

The invention will now be illustrated in greated detail in the following specific Examples, which are given for illustration and not limitation of our invention.

EXAMPLE 1

From immature wheat embryos callus culture was initiated on a culture medium having the following composition:

| RMI: | |
|---|---|
| $NH_4NO_3$ | 6600 mg/lit. |
| $KNO_3$ | 7600 mg/lit. |
| $CaCl_2 \times 2H_2O$ | 1753 mg/lit. |
| $MgSO_4$ (anhydrous) | 723 mg/lit. |
| $KH_2PO_4$ | 680 mg/lit. |
| RMII: | |
| $FeSO_4 \times 7H_2O$ | 557 mg/100 ml |
| EDTA | 745 mg/100 ml |
| RM III: | |
| $H_3BO_3$ | 62 mg/100 ml |
| $MnSO_4 \times 4H_2O$ | 223 mg/100 ml |
| $ZnSO_4 \times 4H_2O$ | 86 mg/100 ml |
| KI | 8.3 mg/100 ml |
| $Na_2MoO_4 \times 2H_2O$ | 2.5 mg/100 ml |
| $CuSO_4 \times 5H_2O$ | 0.25 mg/100 ml |
| $CoCl_2 \times 6H_2O$ | 0.25 mg/100 ml |
| saccharose | 2% (w./v.) |
| agar | 0.8% (w./v.) |
| inosite | 100 mg/lit. |
| 2,4-D | 1 mg/lit. |
| Thiamine (Vitamin $B_1$) | 1 mg/lit. |

For preparing one liter of culture medium 250 ml of RMI stock solution, 5.0 ml of RMII stock solution and 10 ml of RMIII stock solution were used. Components RMI, RMII and RMIII together are called RM-salts [Murashige et al.: Physiol. Plant 15, 473–497 (1962)].

After cultivation for four weeks (1000 lux, 25° C.) the callus cultures were placed on hormone-free culture media, which—apart from inosite—had the same composition as given above but were supplemented with 1, 10 and 100 mg/lit. of silver nitrate, respectively. As a control calli grown on culture media with the same composition but containing no silver nitrate were employed. It has been found that in callus cultures grown on silver nitrate-containing culture media both the regeneration frequency and the average shoot number were significantly better than in the control group. Silver nitrate proved most effective in a 10 mg/lit. concentration. Its effect in Gk-806 wheat cultures is illustrated by the results set forth in Table 1 below.

TABLE 1

The effect of silver nitrate on shoot regeneration in wheat (Gk 806) callus cultures of embryo origin

| $AgNO_3$ (mg/lit.) | Number of calli | Number of regenerating calli | Mean shoot number per regenerating calli |
|---|---|---|---|
| — (control) | 18 | 13 | 2 |
| 10 | 18 | 18 | 6 |

EXAMPLE 2

Essentially following the procedure described in Example 1 but using cobalt chloride as an inhibitor of ethylene action instead of silver nitrate, the following results were obtained.

TABLE 2

The effect of cobalt chloride on shoot regeneration in wheat (Gk 806) callus cultures of embryo origin

| $CoCl_2 \times 6H_2O$ (mg/lit.) | Number of calli | Number of regenerating calli | Mean shoot number per regenerating calli |
|---|---|---|---|
| — | 40 | 16 | 2.8 |
| 5 | 40 | 22 | 3.6 |

EXAMPLE 3

Essentially following the procedure described in Example 1 but using dinitrophenol (DNP) as an inhibitor the following results were obtained.

TABLE 3

The effect of DNP on shoot regeneration in wheat (Gk 806) callus cultures of embryo origin

| DNP (moles) | Number of calli | Number of regenerating calli | Mean shoot number per regenerating calli |
|---|---|---|---|
| — | 36 | 16 | 3.2 |
| $10^{-6}$ | 36 | 20 | 3.7 |

EXAMPLE 4

The procedure described in Example 1 is repeated except that silver nitrate is added to the 2,4-D-containing culture medium used for cultivation of callus cultures. The results obtained are shown in Table 4.

TABLE 4

The effect of silver nitrate on shoot regeneration in wheat (Gk 806) callus cultures of embryo origin cultivated on culture medium containing 0.5 mg/lit. of 2,4-D

| $AgNO_3$ (mg/lit.) | Number of calli | Number of regenerating calli | Mean shoot number per regenerating calli |
|---|---|---|---|
| — | 36 | 5 | 1.4 |
| 10 | 36 | 21 | 5.1 |

EXAMPLE 5

In order to prove that the effect of silver nitrate is based on the inhibition of ethylene action the procedure described in Example 1 was followed, but ethrel(2-chloroethylphosphonic acid) was added to the culture medium. The results are set forth in Table 5 below.

TABLE 5

The effect of ethrel on shoot regeneration in callus cultures of embryo origin (wheat - Avalon)

| 2-chloroethyl-phosphonic acid (mg/lit.) | Number of calli | Number of regenerating calli | Mean shoot number per regenerating calli |
|---|---|---|---|
| — | 40 | 29 | 2.9 |
| 100 | 40 | 19 | 2.2 |

The above results show that, as expected, as a result of ethrel addition the incidence of regeneration in the test cultures has considerably been decreased.

EXAMPLE 6

On a culture medium having the same composition as described in Example 1 but containing 0.5 mg/lit. of 2,4-D instead of 1 mg/lit. of 2,4-D Gk 806 wheat calli were cultivated for seven months. During this time calli completely lost their regeneration ability. Callus cultures were than placed on hormone-free medium, having the above composition, except 2,4-D, to which 10 mg/lit. of silver nitrate were added.

TABLE 6

The effect of silver nitrate on shoot regeneration in wheat callus cultures (Gk 806) of embryo origin, cultivated on a 2,4-D-containing culture medium for a longer period

| AgNO3 (mg/lit.) | Number of calli | Number of regenerating calli |
|---|---|---|
| — | 12 | 0 |
| 10 | 12 | 3 |

It can be seen that calli which have previously lost their regeneration ability became capable of regeneration of a culture medium containing silver nitrate, in other words, silver nitrate induced regeneration.

EXAMPLE 7

From immature millet (Pennisetum americanum) embryos callus culture was induced as described in Example 1 on a culture medium disclosed in Example 1. Callus cultures were placed on hormone-free media after cultivation for four weeks (1000 lx, 25° C.), which either contained silver nitrate (50 mg/lit.) or were silver nitrate-free. Embryogenic calli (which contained embryoids) were inoculated on further media with the same composition after another four-week cultivation period. Shoot formation was observed only on the silver nitrate-containing media.

The results obtained are set forth in Table 7.

TABLE 7

Effect of silver nitrate on shoot regeneration in embryogenic millet callus cultures

| AgNO3 (mg/lit.) | Number of calli | Number of regenerating calli |
|---|---|---|
| — | 12 | 0 |
| 50 | 12 | 12 |

EXAMPLE 8

On nitrate reductase deficient mutants of Nicotiana plumbaginifolia (dicotyledon), the callus culture of which showed no or very poor regeneration ability, the effect of silver nitrate was tested.

The mutant and the control (wild) cell lines were maintained on the culture medium described in Example 1, which was supplemented with the following components:

| benzyl adenine | 1 mg/lit. |
|---|---|
| napthylacetic acid | 0.1 mg/lit. |
| ammonium succinate | 8.25 mmoles |

(see Marton et. al.: Mol.Gen.Genet. 182:301 (1982)).

To induce regeneration naphthylacetic acid was eliminated from this culture medium (on which mutants showed no regeneration at all). On the latter culture medium in case of the mutant cell lines only very poor, accidental regeneration could be achieved. Under the effect of silver nitrate (50 mg/lit.), however, the mutant cell lines practically showed the same regeneration ability as the wild varieties.

| Cell lines | Number of calli | Number of regenerating calli without AgNO3 | 50 mg/lit. AgNO3 |
|---|---|---|---|
| 2/8 + NX9/17A/129 | 14 | 1 | 13 |
| 2/8 + NA9/1F/109 | 14 | 0 | 14 |
| NX21 | 14 | 0 | 14 |
| NA1 | 14 | 0 | 12 |
| NA9 | 14 | 1 | 13 |
| wild variety | 14 | 14 | 14 |

EXAMPLE 9

Tests were carried out to determine the optimum duration of silver nitrate treatment in order to achieve a maximum shoot formation. For this purpose callus cultures were induced from a very poorly regenerating wheat variety (GK Maraton) and from two wheat varieties showing a considerably good regeneration ability (GK Kincso and Avalon). Silver nitrate was added to the culture medium in a concentration of 10 mg/lit. in various points of time: at callus induction, at the first inoculation and at the second inoculation.

As a control cultivation carried out on a silver nitrate-free culture medium was employed. During the inoculations the initial 1 mg/lit. 2,4-D concentration was first reduced to 0.5 mg/lit. and then to zero. Inoculations were performed in one month intervals. The culture medium had the same composition as the culture medium described in Example 1, except silver nitrate and 2,4-D concentrations given above.

If silver nitrate was added to the culture medium during the first or second inoculation, the number of regenerating calli has significantly been increased, particularly in case of the poorly regenerating variety (GK Maraton). If silver nitrate was added to the culture medium during the callus induction already, the ratio of regenerating calli in the poorly regenerating variety has further been increased. Related to the control a 4.4-fold increase can be observed. The numerical results are set forth in Table 9.

It is not only the number of regenerating calli which has been increased, but the shoot number per regenerating callus showed a definite increase as well. The increase in shoot number varied between 75 and 92% depending on the variety.

The improvement of shoot regeneration is especially remarkable if the above two factors are taken into account simultaneously, i.e. the shoot numbers are related to the total number of calli. In this case the increase in shoot regeneration in the poorly regenerating variety is about 8-fold related to the silver nitrate-free control. The effect of silver nitrate in the callus culture of GK Maraton is illustrated on the attached FIGS. 1 and 2.

TABLE 9

Effect of the duration of AgNO3 treatment on the shoot regeneration of calli of immature embryo origin of various wheat varieties

| Start of AgNO3 treatment | Number of inoculi | | | Ratio of regenerating calli (%) | | | Shoot number/ regenerating callus | | | Shoot number/ total number of calli | | |
|---|---|---|---|---|---|---|---|---|---|---|---|---|
| | K | A | M | K | A | M | K | A | M | K | A | M |
| Callus induction | 100 | 90 | 110 | 49 | 59 | 35 | 6.8 | 5.2 | 4.6 | 3.6 | 3.0 | 1.6 |
| First inoculation | 95 | 90 | 100 | 65 | 66 | 20 | 7.0 | 4.4 | 4.9 | 4.5 | 2.9 | 1.0 |
| Second inoculation | 90 | 80 | 80 | 58 | 49 | 14 | 7.5 | 5.9 | 4.9 | 4.3 | 2.9 | 0.7 |
| AgNO3-free control | 90 | 90 | 100 | 52 | 46 | 7 | 3.9 | 3.3 | 2.8 | 2.0 | 1.4 | 0.2 |

K = Kincso variety
A = Avalon variety
M = Maraton variety

EXAMPLE 10

The procedure described in Example 9 was followed except that instead of silver nitrate 5 mg/lit. of cobalt chloride were employed (CoCl$_2$×6H$_2$O), and cobalt chloride was added to the culture medium at callus induction and both subsequent inoculations. Cobalt chloride was sterilized together with the other components of culture medium. As a control cultures cultivated on cobalt chloride-free culture medium were employed. Under the effect of cobalt chloride shoot regeneration was increased in case of all three test varieties: the increase in the ratio of regenerating calli is 20 to 40%, in the shoot number per regenerating callus 15 to 33% and in the shoot number related to the total number of calli 30 to 80%. The shoot regeneration increasing activity of cobalt chloride was, however, somewhat less expressed than that of silver nitrate. The results are shown in Table 10.

TABLE 10

Effect of CoCl$_2$ treatment on shoot regeneration of calli of embryo origin of various wheat varieties

| CoCl$_2$ × 6H$_2$O | Number of inoculi | | | Ratio of regenerating calli (%) | | | Shoot number/ regenerating callus | | | Shoot number/ total number of calli | | |
|---|---|---|---|---|---|---|---|---|---|---|---|---|
| | K | A | M | K | A | M | K | A | M | K | A | M |
| + | 80 | 100 | 60 | 49 | 54 | 12 | 5.4 | 4.3 | 4.0 | 2.5 | 2.3 | 0.5 |
| − (control) | 70 | 70 | 70 | 41 | 39 | 9 | 4.7 | 3.3 | 3.0 | 1.9 | 1.3 | 0.3 |

K = Kincso
A = Avalon
M = Maraton

EXAMPLE 11

To determine the optimum silver nitrate concentration with respect to shoot regeneration calli induced from the three wheat varieties described in Example 9 on a culture medium having the composition described in Example 1 (2,4-D=1 mg/lit.) were used. Silver nitrate was added to the culture medium at the first and second inoculation, in concentrations of 0, 2.5, 5, 10, 20 and 40 mg/lit., respectively. Inoculations were performed in one month intervals, first on a culture medium containing 0.5 mg/lit. of 2,4-D and then on a culture medium without 2,4-D.

Depending on the variety tested 10 mg/lit. and 20 mg/lit. concentrations of silver nitrate proved the most efficient, but in a concentration of 20 mg/lit. silver nitrate has already a slight necrotic effect on the calli. Therefore, in wheat tissue cultures 10 mg/lit. is recommended as an optimum concentration. From the results, which are set forth in Table 11, it can be clearly seen that silver nitrate is effective in a relatively wide concentration range, and there is a sudden increase in shoot regeneration already at the lowest dose tested.

TABLE 11

The effect of AgNO3 concentration of the shoot regeneration of calli of immature embryo origin or various wheat varieties

| AgNO3 concentration (mg/lit.) | Number of inoculi | | | Ratio of regenerating calli (%) | | | Shoot number/ regenerating callus | | | Shoot number/ total number of calli | | |
|---|---|---|---|---|---|---|---|---|---|---|---|---|
| | K | A | M | K | A | M | K | A | M | K | A | M |
| 40 | 92 | 80 | 100 | 51 | 55 | 10 | 6.5 | 4.7 | 3.8 | 3.3 | 2.6 | 0.4 |
| 20 | 90 | 60 | 90 | 63 | 58 | 9 | 6.2 | 4.5 | 4.5 | 3.9 | 3.1 | 0.4 |
| 10 | 40 | 60 | 80 | 58 | 63 | 16 | 6.6 | 4.4 | 5.3 | 3.8 | 2.8 | 0.9 |
| 5 | 50 | 65 | 90 | 54 | 51 | 13 | 6.5 | 4.2 | 4.9 | 3.5 | 2.2 | 0.7 |
| 2.5 | 90 | 63 | 70 | 48 | 51 | 14 | 6.0 | 4.0 | 2.1 | 2.9 | 2.1 | 0.3 |
| − (control) | 81 | 50 | 90 | 40 | 44 | 7 | 3.0 | 2.2 | 2.2 | 1.2 | 1.0 | 0.1 |

K = Kincso
A = Avalon
M = Maraton

EXAMPLE 12

The effect of silver nitrate in the presence of various hormones was tested. In the tests wheat (GK Kincso) calli induced on a culture medium according to Example 1 containing 1 mg/lit. of 2,4-D and maintained at a reduced 2,4-D level (0.5 mg/lit.) were used. The shoot number of calli was determined.

From the data given in Table 12 it can be seen that although 6-benzyl-adenine (BA), which is a known accelerator of shoot regeneration, produced a certain increase in shoot number, its effect has considerably been surpassed by the activity of silver nitrate. Moreover, 6-benzyl-adenine could not compensate the shoot regeneration inhibiting effect of 1-naphthylacetic acid (auxin), in contrary to silver nitrate, which completely compensated the inhibition caused by 1-naphthylacetic acid (NES).

In case of 2,4-D (0.5 mg/lit.), which exerts a very strong shoot regeneration inhibiting effect, the absolute value of shoot regeneration obtained in the presence of silver nitrate is not particularly high but the relative promotion of shoot regeneration is far the strongest in this case (related to the silver nitrate-free control). The interaction of the test hormones and silver nitrate is illustrated in FIG. 3.

TABLE 12

The effect of various hormones and silver nitrate on the shoot regeneration of wheat (GK Kincso) calli of immature embryo origin

| Hormone treatment (mg/lit.) | $AgNO_3$ (mg/lit.) | Number of inoculi | Shoot/inoculum (pieces) |
|---|---|---|---|
| hormone-free (control) | 0 | 36 | 2.0 |
| hormone-free | 10 | 36 | 5.5 |
| BA(1) | 0 | 36 | 3.3 |
| BA(1) | 10 | 36 | 6.0 |
| NES(10) + BA(1) | 0 | 36 | 1.5 |
| NES(10) + BA(1) | 10 | 36 | 5.4 |
| NES(10) | 0 | 36 | 1.4 |
| NES(10) | 10 | 36 | 4.4 |
| 2,4-D (0.5) | 0 | 36 | 0.2 |
| 2,4-D (0.5) | 10 | 36 | 3.0 |

BA = 6-benzyl-adenine
NES = 1-naphthylacetic acid
2,4-D = 2,4-dichlorophenoxyacetic acid

We claim:

1. A process for inducing or increasing shoot regeneration of a cereal or tobacco plant from plant cells cultured in a tissue culture medium which comprises the steps of:
   (a) providing a tissue culture medium comprising a plant hormone and 5 to 100 mg/liter of silver nitrate; and
   (b) forming a tissue culture by cultivating cereal or tobacco plant cells in the tissue culture medium whereby the silver nitrate inhibits ethylene action thereby inducing or increasing shoot regeneration.

2. A process for inducing or increasing shoot regeneration of a cereal or tobacco plant from plant cells cultured in a tissue culture medium which comprises the steps of:
   (a) providing a tissue culture medium comprising a plant hormone;
   (b) forming a tissue culture by cultivating cereal or tobacco plant cells in the tissue culture medium comprising a plant hormone;
   (c) removing the cultivated cereal or tobacco plant cells from the tissue culture medium comprising a plant hormone;
   (d) transferring the cultivated cereal or tobacco plant cells to a hormone-free culture medium containing 5 to 100 mg/l silver nitrate; and
   (e) further cultivating the cereal or tobacco plant cells in the hormone-free tissue culture whereby the silver nitrate inhibits ethylene action thereby inducing or increasing shoot regeneration.

3. A process for inducing or increasing shoot regeneration of a cereal or tobacco plant from plant cells cultured in a tissue culture medium which comprises the steps of:
   (a) providing a tissue culture medium comprising 5 to 100 mg/liter of cobalt chloride; and
   (b) forming a tissue culture by cultivating cereal or tobacco plant cells in the tissue culture medium whereby the cobalt chloride inhibits ethylene production thereby inducing or increasing shoot regeneration.

4. A process for inducing or increasing shoot regeneration of a cereal or tobacco plant from plant cells cultured in a tissue culture medium which comprises the steps of:
   (a) providing a tissue culture medium comprising a plant hormone;
   (b) forming a tissue culture by cultivating cereal or tobacco plant cells in the tissue culture medium comprising a plant hormone;
   (c) removing the cultivated cereal or tobacco plant cells from the tissue culture medium comprising a plant hormone;
   (d) transferring the cultivated cereal or tobacco plant cells to a hormone-free culture medium containing 5 to 100 mg/l cobalt chloride; and
   (e) further cultivating the cereal or tobacco plant cells in the hormone-free tissue culture whereby the cobalt chloride inhibits ethylene production thereby inducing or increasing shoot regeneration.

5. The process defined in claim 1 wherein the hormone contained in the tissue culture medium is a shoot-regenerating inhibiting hormone selected from the group consisting of 1-naphthyl acetic acid and 2,4-dichlorophenoxyacetic acid, and the concentration of $AgNO_3$ is 10 to 100 mg/liter.

6. The process defined in claim 1 wherein the hormone contained in the tissue culture medium is a shoot-regenerating accelerating hormone which is 6-benzyl-adenine.

7. The process defined in claim 1 wherein in step (a) the silver nitrate is added to the tissue culture medium in a concentration of 10 to 20 mg/liter.

8. The process defined in claim 3 wherein in step (a) the cobalt chloride is added to the tissue culture medium in a concentration of 5 mg/liter, in the form of $CoCl_2 \times 6H_2O$.

9. The process defined in claim 3 wherein the hormone contained in the tissue culture medium is a shoot-regenerating accelerating hormone which is 6-benzyl-adenine.

* * * * *